United States Patent
Cheng et al.

(10) Patent No.: US 9,356,244 B1
(45) Date of Patent: May 31, 2016

(54) AMINOFERROCENE DERIVATIVE AND TANDEM ORGANIC LIGHT-EMITTING DIODE CONTAINING THE SAME

(71) Applicant: NATIONAL TSING HUA UNIVERSITY, Hsinchu (TW)

(72) Inventors: Chien-Hong Cheng, Hsinchu (TW); Cheng-Chang Lai, Hsinchu (TW); Yu-Wei Chang, Hsinchu (TW); Chuang-Yi Liao, Taichung (TW); Min-Jie Huang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/927,663

(22) Filed: Oct. 30, 2015

(30) Foreign Application Priority Data

Jul. 1, 2015 (TW) .............................. 104121302 A (51) Int. Cl.
*C07F 15/02* (2006.01)
*H01L 51/00* (2006.01)
*H01L 51/52* (2006.01)

(52) U.S. Cl.
CPC ............ *H01L 51/0083* (2013.01); *C07F 15/02* (2013.01); *H01L 51/5278* (2013.01)

(58) Field of Classification Search
CPC .......................... C07F 15/02; H01L 51/0083
USPC ....................................................... 556/145
See application file for complete search history.

(56) References Cited

U.S. PATENT DOCUMENTS 7,959,693 B2   6/2011  Parish et al.

FOREIGN PATENT DOCUMENTS

TW    2 497 775  A1    9/2012
TW    201425439  A     7/2014

OTHER PUBLICATIONS

Mendiratta et al., Organometallics, vol. 18, No. 3, pp. 454-456 (1999).*
Britton et al., Organometallics, vol. 5, No. 5, pp. 1029-1031 (1986).*

* cited by examiner

*Primary Examiner* — Porfirio Nazario Gonzalez
(74) *Attorney, Agent, or Firm* — Birch, Stewart, Kolasch & Birch, LLP

(57) ABSTRACT

An aminoferrocene derivative is represented by the formula (I):

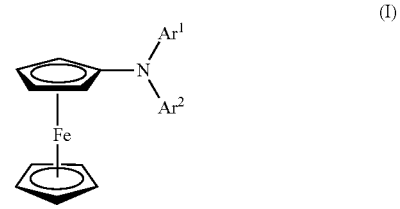

wherein $Ar^1$ and $Ar^2$ independently represent a substituted or unsubstituted $C_6$-$C_{10}$ aryl group. The aminoferrocene derivative is useful for forming a p-type carrier generation layer of a tandem OLED so that the tandem OLED has superior luminous efficiencies in terms of maximum luminance, maximum external quantum efficiency, maximum current efficiency, etc.

4 Claims, 4 Drawing Sheets

AMINOFERROCENE DERIVATIVE AND TANDEM ORGANIC LIGHT-EMITTING DIODE CONTAINING THE SAME

CROSS-REFERENCE TO RELATED APPLICATION

This application claims priority of Taiwanese Application No. 104121302, filed on Jul. 1, 2015.

FIELD

This disclosure relates to an aminoferrocene derivative and a tandem organic light-emitting diode including the aminoferrocene derivative.

BACKGROUND

Organic light-emitting diodes (referred to as OLEDs hereinafter) have advantages such as self-emission, high contrast, high luminance, wide viewing angle and fast response, and thus have been widely used in displays. As compared to a conventional single OLED unit, a tandem OLED, which consists of two or more OLED units connected in series, may achieve the same luminance as that of the conventional single OLED unit at a relatively low current density, and thus has a relatively long service life. In addition, the colors of lights emitted by the respective OLED units of the tandem OLED may be adjusted individually, and thus the tandem OLED is suitable for emitting white light.

The tandem OLED includes a p-type carrier generation layer for generating holes. It is disclosed, for example, in *J. Mater. Chem.*, 2011, 21, pp. 15332-15336, that a thiophene derivative is used for forming the p-type carrier generation layer of the tandem OLED. However, few literature has discussed in detail materials that can serve as the p-type carrier generation layer of the tandem OLED and how such materials can be used to modify the luminance, the external quantum efficiency, the current efficiency and the like of the tandem OLED.

Therefore, there is still a need in the art to develop a novel compound for the p-type carrier generation layer of the tandem OLED in order to enhance the luminance, the external quantum efficiency, the current efficiency and the like of the tandem OLED as compared to the conventional single OLED unit.

SUMMARY

A first object of this disclosure is to provide an aminoferrocene derivative for a p-type carrier generation layer of a tandem OLED so as to enhance the luminance, the external quantum efficiency, the current efficiency and the like of the tandem OLED as compared to a conventional single OLED unit.

A second object of this disclosure is to provide a tandem organic light-emitting diode which includes a p-type carrier generation layer formed from the aminoferrocene derivative.

According to a first aspect of this disclosure, there is provided an aminoferrocene derivative represented by formula (I):

wherein
$Ar^1$ and $Ar^2$ independently represent a substituted or unsubstituted $C_6$-$C_{10}$ aryl group.

According to a second aspect of this disclosure, there is provided a tandem organic light-emitting diode which includes a p-type carrier generation layer formed from the aminoferrocene derivative.

The effect of this disclosure resides in that the molecular weight and the thermal stability of the aminoferrocene derivative of this disclosure is enhanced by the electron-donating group of —$NAr_1Ar_2$ contained therein so that the aminoferrocene derivative has a relatively high HOMO level as compared to that of conventional organic semiconductor materials. Therefore, the aminoferrocene derivative of this disclosure may be used for forming a p-type carrier generation layer of a tandem OLED so that the tandem OLED has enhanced luminance, external quantum efficiency, current efficiency and the like as compared to a conventional single OLED unit.

BRIEF DESCRIPTION OF THE DRAWINGS

Other features and advantages of this disclosure will become apparent in the following detailed description of the embodiments with reference to the accompanying drawings, of which.

DETAILED DESCRIPTION

Aminoferrocene Derivative:

An aminoferrocene derivative according to this disclosure is represented by formula (I):

wherein
$Ar^1$ and $Ar^2$ independently represent a substituted or unsubstituted $C_6$-$C_{10}$ aryl group.

Preferably, $Ar^1$ and $Ar^2$ independently represent a substituted or unsubstituted phenyl.

More preferably, $Ar^1$ and $Ar^2$ independently represent a para-substituted or unsubstituted phenyl.

More preferably, $Ar^1$ and $Ar^2$ independently represent a phenyl group substituted with at least one (preferably one) substituent selected from the group consisting of a substituted or unsubstituted $C_1$-$C_7$ alkyl group, an unsubstituted phenyl group, a diphenylamino-substituted phenyl group, and a ferrocenyl group. Preferably, the substituent includes an unsubstituted $C_1$-$C_7$ alkyl group and a substituted or unsubstituted phenyl. More preferably, the substituent includes a methyl group, an unsubstituted phenyl, and a phenyl group substituted with a diphenylamino group.

Examples of the aminoferrocene derivative illustrated in following examples include compounds Fc01, Fc02, Fc03, and Fc04:

Fc01

Fc02

Fc03

Fc04 wherein Ph represents a phenyl group.

Production of Aminoferrocene Derivative:

The aminoferrocene derivative of this disclosure is produced by subjecting an aminoferrocene compound and a halo-substituted aromatic compound to a reaction in the presence of a catalyst, a solvent and a base.

The halo-substituted aromatic compound used in the following illustrated examples includes 4-bromobiphenyl, 4-iodotoluene, and 4'-bromo-N,N-diphenylbiphenyl-4-amine.

Preferably, the catalyst is a palladium catalyst, which is formed from a palladium compound and a ligand.

In the following illustrated examples, the palladium compound is palladium acetate ($Pd(OAc)_2$) or bis(dibenzylideneacetone)palladium ($Pd(dba)_2$), and the ligand is 1,1'-bis(diphenylphosphio)ferrocene (dppf), 2-dicyclohexylphosphino-2',6'-di-Isopropoxybiphenyl (RuPhos), or tributyl-phosphine.

The solvent used in the following illustrated examples is toluene.

The base used in the following illustrated examples is sodium tert-butoxide (NaO$^t$Bu).

The following examples are provided to illustrate the embodiments of the disclosure, and should not be construed as limiting the scope of the disclosure.

Preparation Example 1

Preparation of Aminoferrocene

Scheme I

Under a nitrogen atmosphere, ferrocene (10 g, 53.8 mmol) was dissolved in anhydrous n-hexane (50 ml), followed by adding and mixing with tetramethylethylenediamine (TMEDA, 18.1 ml, 84.5 mmol) A solution of n-butyllithium (n-BuLi) in n-hexane (2.5 M, 48.0 ml) was added slowly dropwise at 0° C., followed by stirring at 25° C. After stirring for 12 hours and removing the solvent, a light orange yellow complex was formed. The complex was added to anhydrous ethyl ether (200 ml), followed by stirring to disperse the complex in anhydrous ethyl ether and lowering the temperature of the dispersion to −78° C. A solution of iodine (19.0 g) in ethyl ether (350 ml) was added to the dispersion slowly dropwise, and the temperature was raised to 25° C. After stirring for a further hour, the reaction was poured into an aqueous ferric chloride ($FeCl_3$) solution (5 wt %, 100 ml), followed by extraction with ethyl ether (200 ml). An organic layer thus obtained was washed ten times with an aqueous ferric chloride ($FeCl_3$) solution (5 wt %, 100 ml) and then was washed with water until the aqueous layer was clear. Thereafter, water was removed using anhydrous $MgSO_4$ and solvent was also removed to obtain a mixture in the form of a blackish brown liquid of compound a and compound b as shown in scheme I in a molar ratio of 1:1.

The obtained mixture (2.5 g, 6.67 mmol), cuprous iodide (CuI, 128 mg, 0.67 mmol), ferric chloride ($FeCl_3$, 107 mg, 0.67 mmol), sodium hydroxide (NaOH, 540 mg, 13.3 mmol), aqueous ammonia (15 M, 30 ml), and ethanol (EtOH, 30 ml) were placed in a high pressure reaction tube of 150 ml. A reaction was conducted at 90° C. for 12 hours. After the temperature of the content in the reaction dropped to 25° C., ethyl ether (200 ml) was added and the content in the reaction tube was washed three times with an aqueous sodium hydroxide solution (1.0 M, 150 ml). Then, water was removed using anhydrous $MgSO_4$ and solvent was also removed to obtain an orange brown crude product, which was purified by column chromatography (eluent: ethyl acetate/n-hexane=1/2 (v/v)) to obtain aminoferrocene compound c shown in Scheme I in the form of a yellowish brown solid (yield: 48%).

$^1$H NMR (400 MHz, $CDCl_3$) of aminoferrocene compound c: δ 4.08 (s, 5H), 3.97 (t, J=1.6, 2H), 3.82 (t, J=1.6, 2H), 2.58 (br, 2H).

Example 1

Preparation of Aminoferrocene Derivative (Fc01)

Preparation of Compound BPAFc:

The aminoferrocene compound (300 mg, 1.49 mmol) obtained in Preparation Example 1, 4-bromobiphenyl (380 mg, 1.64 mmol), palladium acetate ($Pd(OAc)_2$, 17 mg, 0.075 mmol), 1,1'-bis(diphenylphosphino)ferrocene (dppf, 67 mg, 0.12 mmol), and sodium tert-butoxide ($NaO^tBu$, 577 mg, 6 mmol) were mixed in toluene (5 ml, as a solvent). A reaction was conducted at 90° C. for 72 hours. The reaction was poured into pure water and was extracted five times with ethyl ether (60 ml). The organic layer thus obtained was dried using anhydrous magnesium sulfate. After the solvent was removed, purification was conducted by column chromatography (eluent: n-butane/ethyl acetate=3/2 (v/v)) to obtain compound BPAFc in the form of an orange solid (yield: 68%). The structure of compound BPAFc is shown in Scheme II.

Preparation of Compound Fc01:

Compound BPAFc (100 mg, 0.283 mmol) thus obtained, 4-iodotoluene (123 mg, 0.566 mmol), bis(dibenzylideneacetone)palladium ($Pd(dba)_2$, 4 mg, 0.007 mmol), 2-dicyclohexylphosphino-2',6'-diisopropoxybiphenyl (RuPhos, 7 mg, 0.015 mmol), and sodium tert-butoxide ($NaO^tBu$, 109 mg, 1.13 mmol) were mixed in toluene (3 ml, as a solvent). A reaction was conducted at 130° C. for 72 hours. Pd(dba)$_2$ was filtered using diatomaceous earth and silica gel. The reaction was washed using ethyl acetate and the solvent was removed. Purification was conducted by column chromatography (eluent: n-hexane/ethyl acetate=3/1 (v/v)), followed by sublimation (two times) to obtain compound Fc01 in the form of an orange red solid (yield: 80%).

Analysis for compound BPAFC: $^1$H NMR (400 MHz, CDCl$_3$): δ 7.54 (d, J=8.0 Hz, 2H), 7.45 (d, J=8.8 Hz, 2H), 7.38 (t, J=8.0 Hz, 2H), 7.25 (t, J=7.6 Hz, 1H), 6.95 (d, J=8.8 Hz, 2H), 4.99 (br, 1H), 4.27 (s, 2H), 4.20 (s, 5H), 4.05 (s, 2H); $^{13}$C NMR (100 MHz. CDCl$_3$): δ 141.0, 131.8, 128.9, 128.7, 127.7, 126.9, 126.4, 126.3, 114.9, 68.9, 64.6 and 62.0; HRMS (EI$^+$, m/z) calculated for C$_{22}$H$_{19}$NFe: 353.0867. found: 353.0869.

Analysis for compound Fc01: $^1$H NMR (400 MHz. CDCl$_3$): δ 7.55 (dd, J=8.0, 0.8 Hz, 2H), 7.47 (dd, J=8.0, 2.0 Hz, 2H), 7.37 (t, J=8.0 Hz, 2H), 7.30-7.23 (m, 3H), 7.21 (q, J=6.0 Hz, 4H), 4.15 (s, 5H), 4.30 (t, J=1.6, 2H), 4.10 (t, J=2.0, 2H), 2.36 (s, 3H); $^{13}$C NMR (100 MHz. CDCl$_3$): δ 147.2, 144.6, 140.8, 134.2, 133.8, 130.0, 128.7, 127.4, 126.7, 126.6, 121.8, 106.9, 68.9, 63.9, 60.1 and 21.0; HRMS (EI$^+$, m/z) calculated for C$_{29}$H$_{25}$NFe: 443.1336. found: 443.1339.

Preparation Example 2

Preparation of Aminoferrocene Derivative (Fc02)

Scheme III

Preparation of Compound DPABPAFc:

The aminoferrocene compound (300 mg, 1.5 mmol) obtained in Preparation Example 1,4'-bromo-N,N-diphenylbiphenyl-4-amine (1.8 g, 4.5 mmol), palladium acetate (Pd(OAc)$_2$, 17 mg, 0.075 mmol), a solution of tributylphosphine in n-hexane (0.1 ml, 10 wt %), and sodium tert-butoxide (NaOtBu, 1.13 g, 11.8 mmol) were mixed in toluene (6 ml, as a solvent). A reaction was conducted at 130° C. for 72 hours. Pd(dba)$_2$ was filtered using diatomaceous earth and silica gel. The reaction was washed using ethyl acetate and the solvent was removed. Purification was conducted by column chromatography (eluent: n-hexane/ethyl acetate in a gradient from 4/1 to 3/2 (v/v)) to obtain compound DPABPAFc (yield: 50%). The structure of compound DPABPAFc is shown in scheme III.

Preparation of Compound Fc02:

Compound Fc02 was prepared by a process similar to that for preparing compound DPABPAFc except that the amount of 4'-bromo-N,N-diphenylbiphenyl-4-amine was 7.90 g (19.7 mmol) and that sublimation (two times) was conducted after column chromatography. Compound Fc02 was obtained in the formed of a red solid (yield: 40%).

Analysis for compound DPABPAFc: $^1$H NMR (400 MHz. CDCl$_3$): δ 7.42 (t, J=8.0 Hz, 4H), 7.24 (t, J=8.0 Hz, 4H), 7.11 (d, J=8.0 Hz, 4H), 7.00 (t, J=7.2 Hz, 2H), 6.92 (d, J=7.6 Hz, 2H), 4.89 (br, 1H), 4.29 (s, 2H), 4.21 (s, 5H), 4.08 (s, 2H); $^{13}$C NMR (100 MHz. CDCl$_3$): δ 147.8, 146.2, 141.9, 135.3, 131.2, 129.2, 127.2, 127.0, 124.4, 124.1, 122.6, 115.1, 69.0, 64.7, and 61.8; HRMS (EI$^+$, m/z) calculated for C$_{34}$H$_{28}$N2Fe: 520.1602. found: 520.1599.

Analysis for compound Fc02: $^1$H NMR (400 MHz. CDCl$_3$): δ 7.52 (d, J=8.4 Hz, 4H), 7.46 (d, J=8.8 Hz, 4H), 7.33 (d, J=8.4 Hz, 4H), 7.27-7.23 (m, 8H), 7.11 (d, J=8.4 Hz, 8H), 7.02 (d, J=8.0 Hz, 4H), 4.17 (s, 5H), 4.11 (s, 2H), 4.04 (s, 2H); $^{13}$C NMR (100 MHz. CDCl$_3$): δ 147.7, 147.7, 146.5, 141.9, 135.0, 129.2, 127.5, 127.4, 127.2, 124.5, 124.3, 124.2, 124.0, 122.8, 122.7, 118.0, 69.0, 64.0, and 60.4; HRMS (FAB$^+$, m/z) calculated for C$_{58}$H$_{46}$N3Fe: 840.3041. found: 840.3044.

Example 3

Preparation of Aminoferrocene Derivative (Fc03)

Scheme IV

DPABPAFc

The process for preparing compound Fc01 in Example 1 was repeated except that compound BPAFc was replaced with compound DPABPAFc (132 mg, 0.283 mmol) obtained in Example 2 and that n-hexane/ethyl acetate in a gradient from 3/1 to 1/1 (v/v) was used as eluent in the purification process via column chromatography which was followed by sublimation (two times). Compound Fc03 was obtained in the form of an orange red solid (yield: 55%).

Analysis for compound Fc03: $^1$H NMR (400 MHz. CDCl$_3$): δ 7.43 (t, J=8.0 Hz, 4H), 7.26-7.16 (m, 8H), 7.11-7.02 (m, 5H), 7.00 (t, J=7.6 Hz, 2H), 4.15 (s, 5H), 4.01 (s, 2H), 4.00 (s, 2H), 2.35 (s, 3H); $^{13}$C NMR (100 MHz. CDCl$_3$): δ 147.7, 146.8, 146.5, 134.9, 134.0, 133.6, 129.9, 129.4, 129.2, 127.2, 126.9, 126.8, 126.4, 124.2, 124.1, 122.7, 122.3, 68.8, 63.8, 60.0, and 21.0.

Example 4

Preparation of Aminoferrocene Derivative (Fc04

Scheme V

The process for preparing compound BPAFc in Example 1 was repeated except that 4-bromopiphenyl was used in an amount of 840 mg (3.61 mmol) and that n-hexane/ethyl acetate in a ratio of 3/1 (v/v) was used as eluent in the purification process via column chromatography which was followed by sublimation (two times). Compound Fc04 was obtained in the form of a red solid (yield: 42%).

Analysis for compound Fc04: $^1$H NMR (400 MHz. CDCl$_3$): δ 7.60-7.55 (m, 8H), 7.42 (t, J=8.0 Hz, 4H), 7.34 (d, J=8.4 Hz, 4H), 7.31 (t, J=7.6 Hz, 2H), 4.18 (s, 5H), 4.10 (s, 2H), 4.05 (s, 2H); $^{13}$C NMR (100 MHz. CDCl$_3$): δ 146.8, 140.6, 135.7, 128.8, 127.7, 126.9, 126.8, 124.5, 69.0, 64.0, and 60.5.

Measurement of HOMO and LUMO Level Values for Compounds Fc01, Fc02, Fc03 and Fc04:

HOMO and LUMO level values for each of compounds Fc01, Fc02, Fc03 and Fc04 obtained in Examples 1-4 was measured using a cyclic voltammeter (CH Instruments), a photoelectron spectroscope (AC-2) and an ultraviolet photoelectron spectroscope (NSRRC beamline 24A1). The results are shown in Table 1.

TABLE 1

|  | Fc01 | Fc02 | Fc03 | Fc04 |
|---|---|---|---|---|
| LUMO/HOMO (eV/eV) by CV | 2.0/4.4 | 2.1/4.4 | 2.1/4.4 | 2.1/4.4 |
| LUMO/HOMO (eV/eV) by AC-2 | 2.7/5.1 | 3.0/5.3 | 2.8/5.1 | 2.9/5.2 |
| LUMO/HOMO (eV/eV) by UPS | 3.0/5.4 | 2.9/5.2 | 2.8/5.1 | 3.0/5.3 |

Application Example 1

A tandem OLED having structure I was manufactured in which a p-type carrier generation layer was formed from compound Fc03.

Structure I:

ITO(150)/NPB(50)/TCTA:4 wt%Ir(piq)$_3$(30)/BPhen(20)/BPhen:6 wt%LiF(5)/Al(1)/C$_{60}$(4)/Fc03(1)/MoO$_3$(1)/NPB(50)/TCTA:4 wt%Ir(ppy)$_3$(30)/BPhen(20)/LiF(1)/Al (100)

Figure 1:
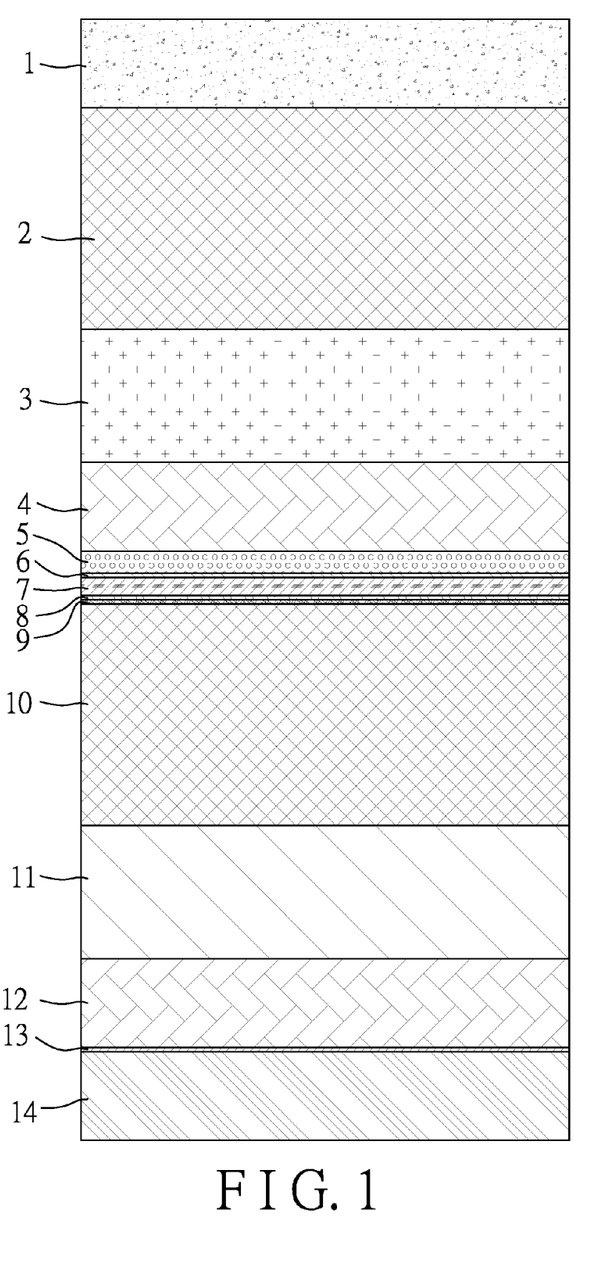
FIG. 1 is a schematic sectional view of a tandem OLED of Application Example 1 according to this disclosure.

The numerical values in brackets indicate thicknesses (nm) of the layers in structure I. Structure I was also schematically illustrated in FIG. 1. The elements denoted by the reference numbers 1-14 in FIG. 1 are set forth in Table 2 below. The materials and thicknesses of the layers shown in FIG. 1 are also indicated in Table 2.

TABLE 2

| Ref. Nos. | | Materials | Thickness (nm) |
|---|---|---|---|
| 1 | Anode | ITO | 150 |
| 2 | Hole transport layer | NPB | 50 |
| 3 | Emissive layer | TCTA doped with 4 wt % Ir(piq)$_3$ | 30 |
| 4 | Electron transport layer | BPhen | 20 |
| 5 | Electron injection layer | BPhen doped with 6 wt % LiF | 5 |
| 6 | Electron injection layer | Al | 1 |
| 7 | n-type carrier generation layer | C$_{60}$ | 4 |
| 8 | p-type carrier generation layer | Compound Fc03 (Example 3) | 1 |
| 9 | Hole injection layer | MoO$_3$ | 1 |
| 10 | Hole transport layer | NPB | 50 |

TABLE 2-continued

| Ref. Nos. | Materials | | Thickness (nm) |
|---|---|---|---|
| 11 | Emissive layer | TCTA doped with 4 wt % Ir(ppy)₃ | 30 |
| 12 | Electron transport layer | BPhen | 20 |
| 13 | Cathode | LiF | 1 |
| 14 | Cathode | Al | 100 |

The abbreviations for the materials indicated in Table 2 are explained as follows.

ITO: indium tin oxide;

NPB: N,N'-bisphenyl-N,N'-bis(1-naphthalenyl)-1,1'-biphenyl-4,4'-diamine];

TCTA: tris(4-carbazoyl-9-yl-phenyl)amine]

TCTA

Ir(piq)₃: tris(1-phenyl-isoquinoline)iridium(III)];

Ir(piq)₃

BPhen: 4,7-diphenyl-1,10-phenanthroline);

BPhen

MoO₃: molybdenum trioxide);

Ir(ppy)₃: tris(2-phenyl-pyridine)iridium(III)].

Ir(ppy)₃

Application Example 2

A tandem OLED having structure II was manufactured in which a p-type carrier generation layer was formed from compound Fc03.

Structure II:
ITO(150)/NPB(50)/TCTA:4 wt%Ir(ppy)₃(30)/BPhen(20)/BPhen:6 wt%LiF(5)/Al(1)/C₆₆(4)/Fc03(1)/MoO(1)/NPB(50)/TCTA:4 wt%Ir(piq)₃(30)/BPhen(20)/LiF(1)/Al (100)

The numerical values in brackets indicate thicknesses (nm) of the layers in structure II. The tandem OLED of Application Example 2 has the same layer structure as that of the tandem OLED of Application Example 1 schematically shown in FIG. 1 except that in Application Example 2, the emissive layer 3 is formed from TCTA doped with 4 wt % Ir(ppy)₃ and the emissive layer 11 is formed from TCTA doped with 4 wt % Ir(pig)₃.

Application Example 3

A tandem OLED having structure III was manufactured in which a p-type carrier generation layer was formed from compound Fc04.

Structure III:
ITO(150)/NPB(50)/TCTA:4 wt%Ir(ppy)₃ (30)/BPhen(20)/BPhen:6 wt%LiF(5)/Al(1)/C₆₀(4)/Fc04(1)/MO₃(1)/NPB(50)/TCTA:4 wt%Ir(ppy)₃(30)/BPhen(20)/LiF(1)/Al (100)

The numerical values in brackets indicate thicknesses (nm) of the layers in structure III. The tandem OLED of Application Example 3 has the same layer structure as that of the tandem OLED of Application Example 1 schematically shown in FIG. 1 except that in Application Example 3, the emissive layer 3 is formed from TCTA doped with 4 wt % Ir(ppy)₃ and the p-type carrier generation layer 8 is formed from compound Fc04 prepared in Example 4.

Application Example 4

A tandem OLED having structure IV was manufactured in which a p-type carrier generation layer was formed from compound Fc04.

Structure IV:

ITO(150)/NPB(50)/TCTA:4 wt%Ir(piq)$_3$(30)/BPhen(20)/BPhen:6 wt%LiF(5)/Al(1)/C$_{60}$(4)/Fc04(1)/MO$_3$(1)/NPB(50)/TCTA:4 wt%Ir(ppy)$_3$(30)/BPhen(20)/LiF(1)/Al(100)

The numerical values in brackets indicate thicknesses (nm) of the layers in structure IV. The tandem OLED of Application Example 4 has the same layer structure as that of the tandem OLED of Application Example 1 schematically shown in FIG. 1 except that in Application Example 4, the p-type carrier generation layer 8 is formed from compound Fc04 prepared in Example 4.

Application Example 5

A tandem OLED having structure V was manufactured in which a p-type carrier generation layer was formed from compound Fc04.

Structure V:

ITO(150)/NPB(30)/TCTA(20)/TCTA:TPBi:8wt%Ir(ppy)$_3$(30)/TPBi(60)/TPBi:6wt%LiF(5)/Al(1)/C$_{60}$(4)/Fc04(1)/MoO$_3$(1)/NPB(30)/TCTA(20)/TCTA:TPBi:8wt%Ir(ppy)$_3$/TPBi(60)/LiF(1)/Al(100)

Figure 2:
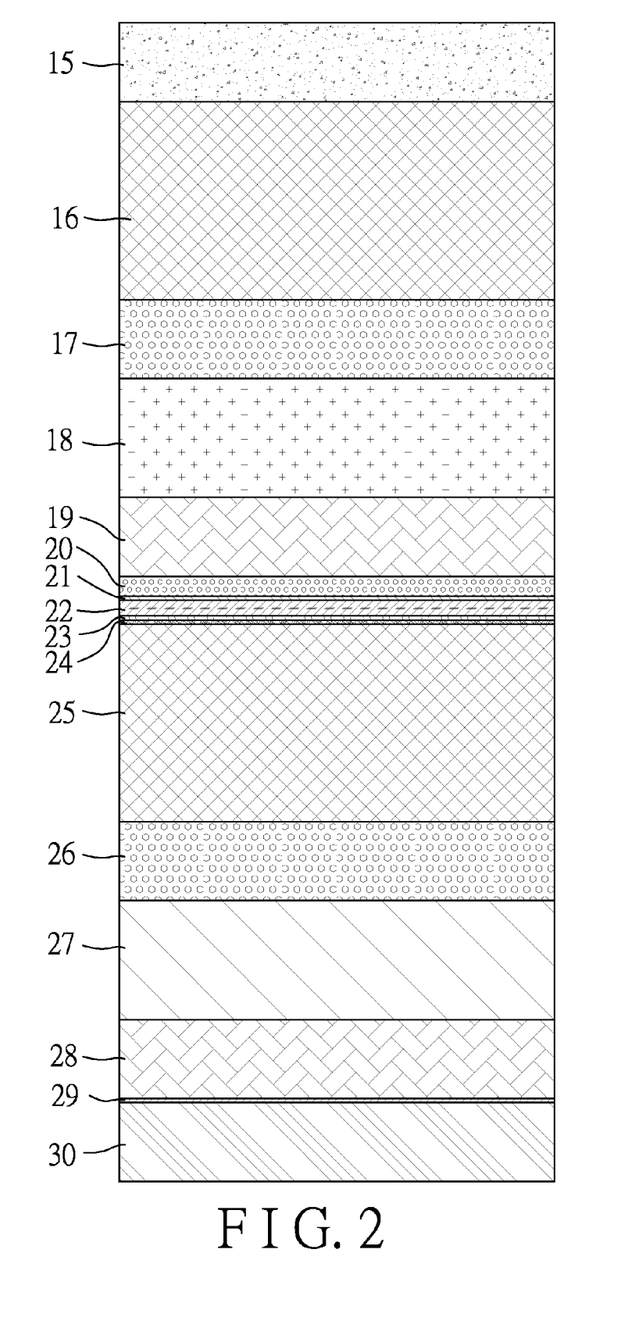
FIG. 2 is a schematic sectional view of a tandem OLED of Application Example 5 according to this disclosure.

The numerical values in brackets indicate thicknesses (nm) of the layers in structure V. Structure V was also schematically illustrated in FIG. 2. The elements denoted by the reference numbers 15-30 in FIG. 2 are set forth in Table 3 below. The materials and thicknesses of the layers shown in FIG. 2 are also indicated in Table 3.

TABLE 3

| Ref. Nos. | | Materials | Thickness (nm) |
|---|---|---|---|
| 15 | Anode | ITO | 150 |
| 16 | Hole transport layer | NPB | 30 |
| 17 | Hole injection layer | TCTA | 20 |
| 18 | Emissive layer | TCTA/TPBi doped with 8 wt % Ir(ppy)$_3$ | 30 |
| 19 | Electron transport layer | TPBi | 60 |
| 20 | Electron injection layer | TPBi* doped with 6 wt % LiF | 5 |
| 21 | Electron injection layer | Al | 1 |
| 22 | n-type carrier generation layer | C$_{60}$ | 4 |
| 23 | p-type carrier generation layer | Compound Fc04 (Example 4) | 1 |
| 24 | Hole injection layer | MoO$_3$ | 1 |
| 25 | Hole transport layer | NPB | 30 |
| 26 | Hole injection layer | TCTA | 20 |
| 27 | Emissive layer | TCTA/TPBi doped with 8 wt % Ir(ppy)$_3$ | 30 |
| 28 | Electron transport layer | TPBi | 60 |
| 29 | Cathode | LiF | 1 |
| 30 | cathode | Al | 100 |

*TPBi: 1,3,5-tris(N-phenylbenzimidizol-2-yl) benzene

TPBi

Application Example 6

A tandem OLED having structure VI was manufactured in which a p-type carrier generation layer was formed from compound Fc01.

Structure VI:

ITO(150)/NPB(30)/TCTA(20)/TCTA:TPBi:8wt%Ir(ppy)(30)/TPBi(60)/TPBi:6wt%LiF(5)/Al(1)/C$_{60}$(4)/Fc01(1)/MoO$_3$(1)/NPB(30)/TCTA(20)/TCTA:TPBi:8wt%Ir(ppy)$_3$/TPBi(60)/LiF(1)/Al(100)

The numerical values in brackets indicate thicknesses (nm) of the layers in structure VI. The tandem OLED of Application Example 6 has the same layer structure as that of the tandem OLED of Application Example 5 schematically shown in FIG. 2 except that in Application Example 6, the p-type carrier generation layer 23 is formed from Fc01 prepared in Example 1.

Application Example 7

A tandem OLED having structure VII was manufactured in which a p-type carrier generation layer was formed from compound Fc03.

Structure VII:

ITO(150)/NPB(30)/TCTA(20)/TCTA:TPBi:8wt%Ir(ppy)$_3$(30)/TPBi(60)/TPBi:6wt%LiF(5)/Al(1)/C$_{60}$(4)/Fc03(1)/MoO$_3$(1)/NPB(30)/TCTA(20)/TCTA:TPBi:8wt%Ir(ppy)$_3$/TPBi (60)/LiF(1)/Al(100)

The numerical values in brackets indicate thicknesses (nm) of the layers in structure VII. The tandem OLED of Application Example 7 has the same layer structure as that of the tandem OLED of Application Example 5 schematically shown in FIG. 2 except that in Application Example 7, the p-type carrier generation layer 23 is formed from Fc03 prepared in Example 3.

Comparative Application Example 1

An OLED unit having structure VIII was manufactured.

Structure VIII:

ITO(150)/NPB(50)/TCTA:4wt%Ir(piq)$_3$(30)/BPhen(20)/LiF(1)/Al(100)

Figure 3:
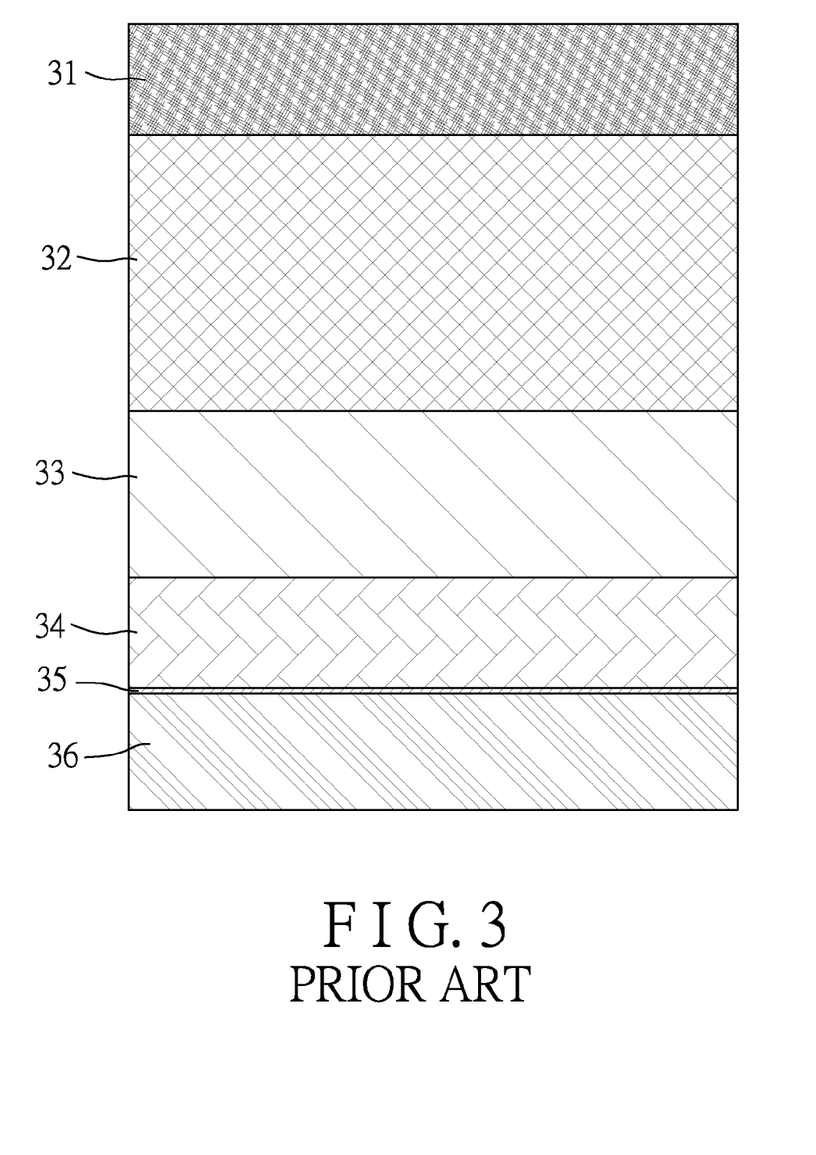
FIG. 3 is a schematic sectional view of an OLED unit of Comparative Application Example 1.

The numerical values in brackets indicate thicknesses (nm) of the layers in structure VIII. Structure VIII was also schematically illustrated in FIG. 3. The elements denote by reference numbers 31-36 in FIG. 3 are set forth in Table 4 below. The materials and thicknesses of the layers shown in FIG. 3 are also indicated in Table 4.

TABLE 4

| Ref. Nos. | | Materials | Thickness (nm) |
|---|---|---|---|
| 31 | Anode | ITO | 150 |
| 32 | Hole transport layer | NPB | 50 |
| 33 | Emissive layer | TCTA doped with 4 wt % Ir(piq)$_3$ | 30 |
| 34 | Electron transport layer | BPhen | 20 |
| 35 | Cathode | LiF | 1 |
| 36 | Cathode | Al | 100 |

Comparative Application Example 2

An OLED unit having structure IX was manufactured.
Structure IX:
ITO(150)/NPB(50)/TCTA:4wt%Ir(ppy)$_3$(30)/BPhen(20)/LiF(1)/Al(100)

The numerical values in brackets indicate thicknesses (nm) of the layers in structure IX. The OLED unit of Comparative Application Example 2 has the same layer structure as that of the OLED unit of Comparative Application Example 1 schematically shown in FIG. 3 except that in Comparative Application Example 2, the emissive layer 33 is formed from TCTA doped with 4 wt % Ir(ppy)$_3$.

Comparative Application Example 3

An OLED unit having structure X was manufactured.
Structure X:
ITO(150)/NPB(30)/TCTA(20)/TCTA:TPBi:8wt%Ir(ppy)$_3$(30)/TPBi(60)/TPBi:6wt%LiF(5)/Al(100)

Figure 4:
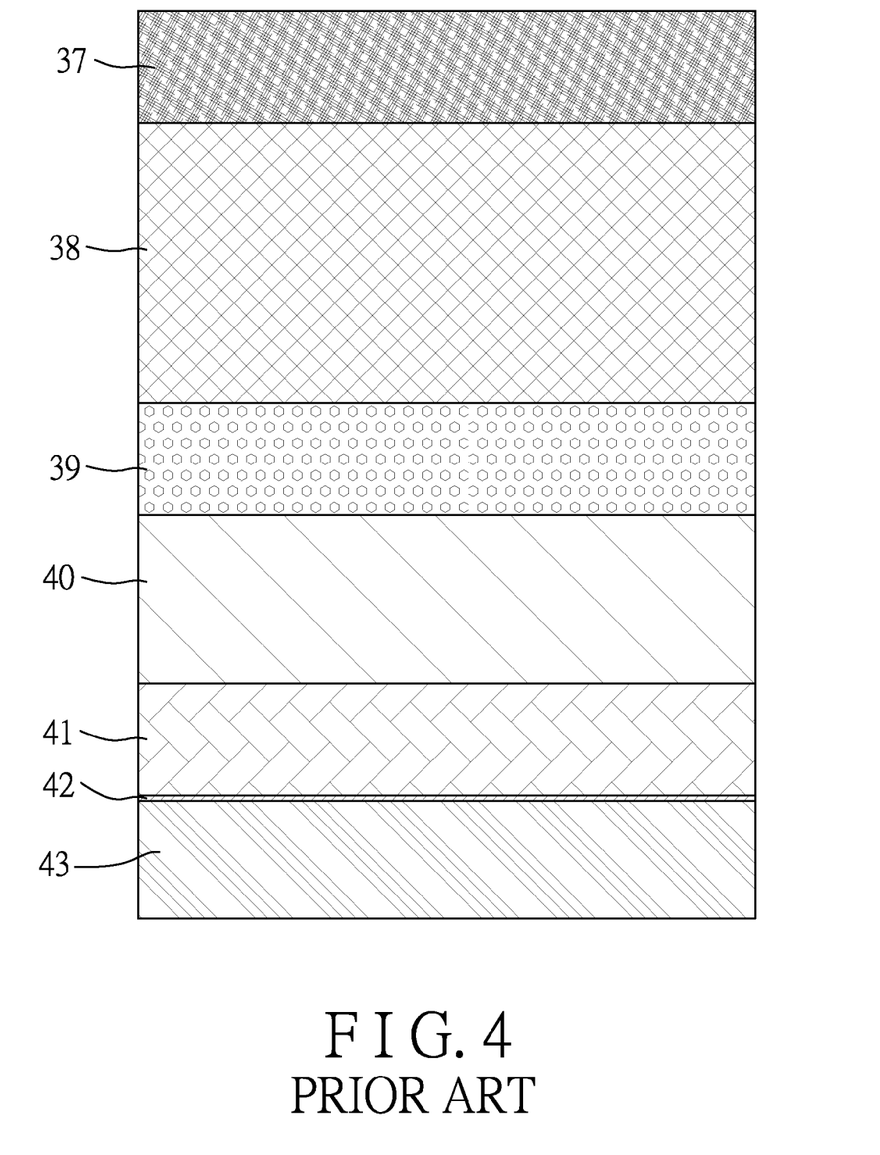
FIG. 4 is a schematic sectional view of an OLED unit of Comparative Application Example 3.

The numerical values in brackets indicate thicknesses (nm) of the layers in structure X. Structure X was also schematically illustrated in FIG. 4. The elements denoted by the reference numbers 37-43 in FIG. 4 are set forth in Table 5 below. The materials and thicknesses of the layers shown in FIG. 4 are also indicated in Table 5.

TABLE 5

| Ref. Nos. | | Materials | Thickness (nm) |
|---|---|---|---|
| 37 | Anode | ITO | 150 |
| 38 | Hole transport layer | NPB | 30 |
| 39 | Hole injection layer | TCTA | 20 |
| 40 | Emissive layer | TCTA/TPBi doped with 8 wt % Ir(ppy)$_3$ | 30 |
| 41 | Electron transport layer | TPBi | 60 |
| 42 | Electron injection layer | TPBi doped with 6 wt % LiF | 5 |
| 43 | cathode | Al | 100 |

Comparative Application Example 4

An OLED unit having structure XI was manufactured.
Structure XI:
ITO(150)/NPB(30)/TCTA(20)/TCTA:TPBi:8wt%Ir(ppy)$_3$(30)/TPBi(60)/LiF(1)/Al(100)

The numerical values in brackets indicate thicknesses (nm) of the layers in structure XI. The OLED unit of Comparative Application Example 4 has the same layer structure as that of the OLED unit of Comparative Application Example 3 schematically shown in FIG. 4 except that in Comparative Application Example 4, the electron injection layer 4 is formed from LiF and has a thickness of 1 nm.

Analysis of HOMO and LUMO Level Values for Application Examples 1-7:

HOMO and LUMO level values for the materials of the layers in each of the tandem OLEDs of Application Examples 1-7 was measured using an ultraviolet photoelectron spectroscope. The results for Application Examples 1-4 are shown in Table 6 below and the results for Application Examples 5-7 are shown in Table 7 below.

TABLE 6

| Materials | HOMO (eV) | LUMO (eV) |
|---|---|---|
| ITO | 4.7 | — |
| NPB | 5.4 | 2.3 |
| TCTA doped with 4 wt % Ir(piq)$_3$ | 5.2 [5.7] | 3.2 [2.4] |
| [TCTA doped with 4 wt % Ir(ppy)$_3$] | 5.3 [5.7] | 2.9 [2.4] |
| BPhen | 6.5 | 3.0 |
| BPhen doped with 6 wt % LiF | 6.5 | 3.0 |
| Al | — | 4.1 |
| C$_{60}$ | 6.2 | 4.5 |
| Compound Fc03 | 5.1 | 2.8 |
| [Compound Fc04] | [5.3] | [3.0] |
| MoO$_3$ | 5.3 | 2.3 |
| NPB | 5.4 | 2.3 |
| TCTA doped with 4 wt % Ir(ppy)$_3$ | 5.3 [5.7] | 2.9 [2.4] |
| [TCTA doped with 4 wt % Ir(piq)$_3$] | 5.2 [5.7] | 3.2 [2.4] |
| BPhen | 6.5 | 3.0 |
| LiF | — | 3.2 |
| Al | — | 3.2 |

TABLE 7

| Materials | HOMO (eV) | LUMO (eV) |
|---|---|---|
| ITO | 4.7 | — |
| NPB | 5.4 | 2.3 |
| TCTA | 5.7 | 2.4 |
| TCTA/TPBi doped with 8 wt % Ir(ppy)$_3$ | 5.6 | 3.0 |
| TPBi | 6.2 | 2.7 |
| TPBi doped with 6 wt % LiF | 6.2 | 2.7 |
| Al | — | 4.1 |
| C$_{60}$ | 6.2 | 4.5 |
| Compound Fc0 4 | 5.3 | 3.0 |
| [Compound Fc01] | [5.4] | [3.0] |
| [Compound Fc03] | [5.1] | [2.8] |
| MoO3 | 5.3 | 2.3 |
| NPB | 5.4 | 2.3 |
| TCTA | 5.7 | 2.4 |

TABLE 7-continued

| Materials | HOMO (eV) | LUMO (eV) |
|---|---|---|
| TCTA/TPBi doped with 8 wt % Ir(ppy)$_3$ | 5.6 | 3.0 |
| TPBi | 6.2 | 2.7 |
| LiF | — | 3.2 |
| Al | — | 3.2 |

As shown in Table 6, the HOMO level values of compound FC03 (Example 3) and compound Fc04 (Example 4) used for the p-type carrier generation layer 8 are respectively 5.1 eV and 5.3 eV, which are close or identical to the HOMO level value (5.3 eV) of MoO$_3$ used for the hole injection layer 9 adjacent to the p-type carrier generation layer 8. Likewise, the LUMO level values of compound FC03 and compound Fc04 used for the p-type carrier generation layer 8 are respectively 2.8 eV and 3.0 eV, which are close to the LUMO level value (2.3 eV) of MoO$_3$ used for the hole injection layer 9 adjacent to the p-type carrier generation layer 8.

In addition, as shown in Table 7, the HOMO level values of compound Fc04 (Example 4), Fc01 (Example 1) and compound Fc03 (Example 3) used for the p-type carrier generation layer 23 are respectively 5.3 eV, 5.4 eV and 5.3 eV, which are close or identical to the HOMO level value (5.3 eV) of MoO$_3$ used for the hole injection layer 24 adjacent to the p-type carrier generation layer 23. Likewise, the LUMO level values of compound FC04, compound FC01 and compound Fc03 for the p-type carrier generation layer 23 are respectively 3.0 eV, 3.0 eV and 2.8 eV, which are close to the LUMO level value (2.3 eV) of MoO$_3$ used for the hole injection layer 24 adjacent to the p-type carrier generation layer 23.

It has thus been demonstrated that compounds Fc01, Fc03 and Fc04, which are examples of the aminoferrocene derivative of this disclosure, are useful as material for forming a p-type carrier generation layer of a tandem OLED.

Measurement of Luminous Efficiencies of the tandem OLEDs of Application Examples 1-4 and the OLED Units of Comparative Application Examples 1 and 2:

The tandem OLEDs of Application Examples 1-4 and the OLED units of Comparative Application Examples 1 and 2 were tested to obtain luminous efficiencies including driving voltage ($V_d$), maximum luminance (L), maximum external quantum efficiency ($\eta_{ext}$), maximum current efficiency ($\eta_C$), maximum power efficiency ($\eta_p$), maximum emission wavelength ($\lambda_{em}$), and CIE coordinates. The results are shown in Table 8. The driving voltage ($V_d$), the maximum luminance (L), the maximum external quantum efficiency ($\eta_{ext}$), the maximum current efficiency ($\eta_c$) and the maximum power efficiency ($\eta_p$) were obtained using an optical meter (Newport 1835-C) and a source measurement unit (Keithley 2400 Source Meter®) equipped with a silicon photodiode (Newport 818-ST). The maximum emission wavelength ($\lambda_{em}$) was obtained using a Hitachi F-4500 fluorescence spectrophotometer.

TABLE 8

| | Appln. Ex. 1 | Appln. Ex. 2 | Appln. Ex. 3 | Appln. Exm. 4 | Comp. Appln. Ex. 1 | Comp. Appln. Ex. 2 |
|---|---|---|---|---|---|---|
| $V_d$ (V) | 4.51 | 4.82 | 4.51 | 4.52 | 2.22 | 2.07 |
| L(cd/m$^2$) | 126471 | 76565 | 90927 | 110958 | 43280 | 59287 |
| [voltage (V)] | [15.0] | [15.5] | [15.5] | [16.0] | [12.5] | [11.5] |
| $\eta_{ext}$ (%) | 27.44 | 14.22 | 19.73 | 26.44 | 6.28 | 10.00 |
| [voltage (V)] | [5.0] | [7.0] | [5.5] | [5.0] | [2.5] | [3.0] |
| $\eta_c$ (cd/A) | 118.85 | 60.10 | 74.71 | 89.80 | 19.68 | 37.88 |
| [voltage (V)] | [5.0] | [7.0] | [5.5] | [5.0] | [2.5] | [3.0] |
| $\eta_p$ (lm/W) | 74.56 | 33.21 | 46.24 | 56.31 | 24.63 | 39.57 |
| [voltage (V)] | [5.0] | [5.5] | [5.0] | [5.0] | [2.5] | [3.0] |
| $\lambda_{em}$ (nm) | 513 | 544 | 514 | 516 | 620 | 514 |
| CIE (x,y) | (0.33, 0.59) | (0.44, 0.54) | (0.29, 0.64) | (0.32, 0.60) | (0.66, 0.34) | (0.26, 0.65) |

As shown in Table 8, the maximum luminance (L), the maximum external quantum efficiency ($\eta_{ext}$) and the maximum current efficiency ($\eta_c$) of the tandem OLEDs of Application Examples 1-4 which individually include a p-type carrier generation layer formed from compound Fc03 or compound Fc04 to serially connect the OLED units of Comparative Application Example 1 or 2 are higher than those of the OLED units of Comparative Application Examples 1 and 2. In addition, as shown in the CIE coordinate data in Table 8, the light emitted by the tandem OLEDs of Application Examples 1-4 is relatively white as compared to the light emitted by the OLED units of Comparative Application Examples 1 and 2. It has thus been demonstrated that the aminoferrocene derivative of this disclosure is useful as a material for forming a p-type carrier generation layer of a tandem OLED so that the tandem OLED has superior luminous efficiencies in terms of maximum luminance (L), maximum external quantum efficiency ($\eta_{ext}$) and maximum current efficiency ($\eta_c$) and may emit white light.

The voltage (V), the maximum luminance (L), the maximum external quantum efficiency ($\eta_{ext}$), the maximum current efficiency ($\eta_c$), and the maximum power efficiency ($\eta_p$) of the tandem OLEDs of Application Examples 1-4 and the OLED units of Comparative Application Examples 1 and 2 were tested under the same current density (J). The results are shown in Table 9 below.

TABLE 9

| | Appln. Ex. 1 | Appln. Ex. 2 | Appln. Ex. 3 | Appln. Ex. 4 | Comp. Appln. Ex. 1 | Comp. Appln. Ex. 2 |
|---|---|---|---|---|---|---|
| J (mA/cm$^2$) | 10 | 10 | 10 | 10 | 10 | 10 |
| V(V) | 8.0 | 8.4 | 8.1 | 8.0 | 3.7 | 3.6 |
| L(cd/m$^2$) | 10016 | 5870 | 6966 | 7881 | 1930 | 3570 |
| $\eta_{ext}$ (%) | 23.13 | 13.89 | 18.42 | 22.88 | 6.17 | 9.54 |
| $\eta_c$ (cd/A) | 100.18 | 58.74 | 69.75 | 78.83 | 19.38 | 36.14 |
| $\eta_p$ (lm/W) | 39.27 | 21.86 | 27.14 | 30.98 | 16.72 | 31.32 |

As shown in Table 9, under the same current density (10 mA/cm$^2$), the maximum luminance (L), the maximum external quantum efficiency ($\eta_{ext}$), and the maximum current efficiency ($\eta_c$) of the tandem OLEDs of Application Examples 1-4 which individually include a p-type carrier generation layer formed from compound Fc03 or compound Fc04 are higher than those of the OLED units of Comparative Application Examples 1 and 2. It has thus been demonstrated that the aminoferrocene derivative of this disclosure is useful as a material for forming a p-type carrier generation layer of a tandem OLED so that the tandem OLED has superior luminous efficiencies in terms of maximum luminance (L), maximum external quantum efficiency ($\eta_{ext}$) and maximum current efficiency ($\eta_c$).

Measurement of Luminous Efficiencies of the Tandem OLEDs of Application Examples 5-7 and the OLED Units of Comparative Application Examples 3 and 4:

The tandem OLEDs of Application Examples 5-7 and the OLEDs of Comparative Application Examples 3 and 4 were tested to obtain luminous efficiencies, including the driving voltage ($V_d$), the maximum luminance (L), the maximum external quantum efficiency ($\eta_{ext}$), the maximum current efficiency ($\eta_c$), the maximum power efficiency ($\eta_p$), the maximum emission wavelength ($\lambda_{em}$), and the CIE coordinates. The results are shown in Table 10 below.

TABLE 10

|  | Appl. Ex. 5 | Appl. Ex. 6 | Appl. Ex. 7 | Comp. Appl. Ex. 3 | Comp. Appl. Ex. 4 |
|---|---|---|---|---|---|
| $V_d$(V) | 5.04 | 5.04 | 5.07 | 2.52 | 2.52 |
| L(cd/m²) [voltage (V)] | 230268 [20.0] | 217222 [19.5] | 214058 [20.0] | 196132 [16.5] | 223930 [13.5] |
| $\eta_{ext}$(%) [voltage V)] | 59.51 [6.5] | 47.11 [5.5] | 48.85 [5.5] | 29.08 [4.0] | 23.55 [6.0] |
| $\eta_c$(cd/A) [voltage V)] | 230.45 [6.5] | 180.95 [9.5] | 187.62 [5.5] | 113.05 [4.0] | 91.56 [6.0] |
| $\eta_p$(lm/W) [voltage (V)] | 119.82 [6.0] | 80.77 [6.5] | 106.95 [5.5] | 100.16 [3.5] | 58.03 [4.5] |
| $\lambda_{em}$(nm) | 518 | 516 | 516 | 516 | 516 |
| CIE (x, y) | (0.31, 0.63) | (0.29, 0.64) | (0.31, 0.63) | (0.29, 0.64) | (0.31, 0.63) |

As shown in Table 10, the maximum external quantum efficiency ($\eta_{ext}$) and the maximum current efficiency ($\eta_c$) of the tandem OLEDs of Application Examples 5-7 which individually include a p-type carrier generation layer formed from compound Fc04, compound Fc01, or compound Fc01 to serially connect the OLED units of Comparative Application Example 3 or 4 are higher than those of the OLED units of Comparative Application Examples 3 and 4. It has thus been demonstrated again that the aminoferrocene derivative of this disclosure is useful as a material for forming a p-type carrier generation layer of a tandem OLED so that the tandem OLED has superior luminous efficiencies in terms of maximum external quantum efficiency ($\eta_{ext}$) and maximum current efficiency ($\eta_c$).

The voltage (V), the maximum luminance (L), the maximum external quantum efficiency ($\eta_{ext}$), the maximum current efficiency ($\eta_c$), and the maximum power efficiency ($\eta_p$) of the tandem OLEDs of Application Examples 5-7 and the OLED units of Comparative Application Examples 3 and 4 were tested under the same current density (J). The results are shown in Table 11 below.

TABLE 11

|  | Appln. Ex. 5 | Appln. Ex. 6 | Appln. Ex. 7 | Comp. Appln. Ex. 3 | Comp. Appln. Ex. 4 |
|---|---|---|---|---|---|
| J (mA/cm²) | 10 | 10 | 10 | 10 | 10 |
| V(V) | 12.2 | 12.6 | 12.7 | 6.4 | 5.4 |
| L(cd/m²) | 20311 | 17489 | 17656 | 10204 | 8576 |
| $\eta_{ext}$(%) | 52.49 | 45.55 | 45.99 | 26.30 | 21.99 |
| $\eta_c$(cd/A) | 203.26 | 174.97 | 176.67 | 102.23 | 85.51 |
| $\eta_p$(lm/W) | 52.42 | 43.65 | 43.73 | 50.21 | 49.41 |

As shown in Table 11, under the same current density (10 mA/cm²), the maximum luminance (L), the maximum external quantum efficiency ($\eta_{ext}$) and the maximum current efficiency ($\eta_c$) of the tandem OLEDs of Application Examples 5-7 which individually include a p-type carrier generation layer formed from compound Fc04, compound Fc01 or compound Fc03 to serially connect the OLED units of Comparative Application Example 3 or 4 are higher than those of the OLED units of Comparative Application Examples 3 and 4. It has thus been demonstrated that the aminoferrocene derivative of this disclosure is useful as a material for forming a p-type carrier generation layer of a tandem OLED so that the tandem OLED has superior luminous efficiencies in terms of maximum luminance (L), maximum external quantum efficiency ($\eta_{ext}$) and maximum current efficiency ($\eta_c$).

In addition, the tandem OLEDs of Application Examples 5-7 and the OLED units of Comparative Application Examples 3 and 4 were tested under the same luminance to obtain the voltage (V), the maximum current density (J), the maximum external quantum efficiency ($\eta_{ext}$), the maximum current efficiency ($\eta_c$), and the maximum power efficiency ($\eta_p$). The results are shown in Table 12 below.

TABLE 12

|  | Appln. Ex. 5 | Appln. Ex. 6 | Appln. Ex. 7 | Appln. Ex. 3 | Appln. Ex. 4 |
|---|---|---|---|---|---|
| L(cd/m²) | 100 | 100 | 100 | 100 | 100 |
| V(V) | 6.3 | 6.8 | 6.6 | 3.3 | 3.2 |
| J (mA/cm²) | 0.043 | 0.058 | 0.057 | 0.091 | 0.427 |
| $\eta_{ext}$(%) | 59.37 | 44.33 | 45.36 | 26.26 | 4.94 |
| $\eta_c$(cd/A) | 229.92 | 170.26 | 174.23 | 102.08 | 19.22 |
| $\eta_p$(lm/W) | 115.27 | 78.81 | 82.96 | 96.09 | 17.78 |

As shown in Table 12, under the same luminance (100 cd/m²), the maximum external quantum efficiency ($\eta_{ext}$) and the maximum current efficiency ($\eta_c$) of the tandem OLEDs of Application Examples 5-7 which include a p-type carrier generation layer formed from compound Fc04, compound Fc01 or compound Fc03 to serially connect the OLED units of Comparative Application Example 3 or 4 are higher than those of the OLED units of Comparative Application Examples 3 and 4. It has thus been demonstrated again that the aminoferrocene derivative of this disclosure is useful as a material for forming a p-type carrier generation layer of a tandem OLED so that the tandem OLED has superior luminous efficiencies in terms of maximum external quantum efficiency ($\eta_{ext}$) and maximum current efficiency ($\eta_c$). It is also shown in Table 12 that, in terms of current density required for obtaining the same luminance, the current density of the tandem OLEDs of Application Examples 5-7 is lower than those of the OLED units of Comparative Application Examples 3 and 4.

In view of the aforesaid, the aminoferrocene derivative of this disclosure is useful as a material for forming a p-type carrier generation layer to serially connect two or more OLED units to form a tandem OLED so that the tandem OLED has superior luminous efficiencies in terms of the maximum luminance, the maximum external quantum efficiency, maximum current efficiency, etc., as compared to the respective OLED units.

While the disclosure has been described in connection with what are considered the exemplary embodiment(s), it is understood that this disclosure is not limited to the disclosed embodiments but is intended to cover various arrangements included within the spirit and scope of the broadest interpretation so as to encompass all such modifications and equivalent arrangements.

What is claimed is:

1. An aminoferrocene derivative represented by formula (I):

(I)

wherein $Ar^1$ and $Ar^2$ independently represent a phenyl group substituted with at least one substituent selected from the group consisting of an unsubstituted phenyl group, a diphenylamino-substituted phenyl group, and a ferrocenyl group.

2. The aminoferrocene derivative according to claim 1, wherein $Ar^1$ and $Ar^2$ independently represent a phenyl which is para-substituted.

3. The aminoferrocene derivative according to claim 1, wherein said at least one substituent is a diphenylamino-substituted phenyl group.

4. A tandem organic light-emitting diode, comprising a p-type carrier generation layer which includes an aminoferrocene derivative represented by formula (I):

(I)

wherein $Ar^1$ and $Ar^2$ independently represent a substituted or unsubstituted $C_6$-$C_{10}$ aryl group.

* * * * *